(12) United States Patent
Park et al.

(10) Patent No.: US 12,311,144 B2
(45) Date of Patent: May 27, 2025

(54) DRUG DELIVERY DEVICE AND METHOD OF OPERATING THE DEVICE

(71) Applicant: Samsung Electronics Co., Ltd., Suwon-si (KR)

(72) Inventors: Kitae Park, Seoul (KR); Joonseong Kang, Suwon-si (KR); Sang Joon Kim, Hwaseong-si (KR); Young Jun Hong, Seoul (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 428 days.

(21) Appl. No.: 17/110,807

(22) Filed: Dec. 3, 2020

(65) Prior Publication Data
US 2022/0047810 A1    Feb. 17, 2022

(30) Foreign Application Priority Data
Aug. 11, 2020  (KR) .................. 10-2020-0100663

(51) Int. Cl.
*A61M 31/00*    (2006.01)
*A61M 5/172*    (2006.01)

(52) U.S. Cl.
CPC ..... *A61M 5/172* (2013.01); *A61M 2205/3306* (2013.01); *A61M 2205/3584* (2013.01); *A61M 2205/3592* (2013.01); *A61M 2205/52* (2013.01); *A61M 2230/201* (2013.01)

(58) Field of Classification Search
CPC ... A61M 5/1723; A61M 31/002; A61F 2/022; A61N 5/062
See application file for complete search history.

(56) References Cited

U.S. PATENT DOCUMENTS

| 5,741,334 | A | * | 4/1998 | Mullon | A61F 2/022 |
|---|---|---|---|---|---|
| | | | | | 424/424 |
| 8,657,804 | B2 | | 2/2014 | Horne et al. | |
| 8,911,426 | B2 | | 12/2014 | Coppeta et al. | |
| 9,101,690 | B2 | | 8/2015 | Deisseroth et al. | |
| 9,642,864 | B2 | | 5/2017 | Murata | |
| 2007/0249007 | A1 | * | 10/2007 | Rosero | A61P 3/10 |
| | | | | | 435/14 |

(Continued)

FOREIGN PATENT DOCUMENTS

| KR | 10-1459192 B1 | 11/2014 |
|---|---|---|
| KR | 10-1496392 B1 | 2/2015 |

(Continued)

OTHER PUBLICATIONS

Extended European Search Report issued on Jan. 13, 2022 in counterpart International European Patent Application No. 21185024.3 (7 pages in English).

*Primary Examiner* — Emily L Schmidt
(74) *Attorney, Agent, or Firm* — NSIP Law (57) ABSTRACT

A drug delivery device and a method of operating the drug delivery device are provided. The drug delivery device includes a light emitter disposed in a body to emit light based on a control signal, a drug reservoir configured to react to the light emitted from the light emitter and to release a drug, a photosensor configured to sense light passing through the drug reservoir, and a controller configured to monitor a degree to which the drug reservoir reacts to the light, based on an amount of light sensed by the photosensor.

23 Claims, 9 Drawing Sheets

(56) References Cited

U.S. PATENT DOCUMENTS

| | | | |
|---|---|---|---|
| 2010/0196439 A1* | 8/2010 | Beck | A61L 27/3616 |
| | | | 424/424 |
| 2011/0311489 A1* | 12/2011 | Deisseroth | A61N 5/062 |
| | | | 536/23.6 |
| 2013/0041343 A1* | 2/2013 | Toumazou | A61M 5/1723 |
| | | | 604/504 |
| 2015/0056143 A1* | 2/2015 | Yun | A61K 47/10 |
| | | | 424/9.6 |
| 2019/0381311 A1* | 12/2019 | Sabiev | A61N 1/30 |
| 2020/0196868 A1 | 6/2020 | Shachar et al. | |
| 2021/0100993 A1* | 4/2021 | Klemm | A61M 5/16809 |
| 2021/0220558 A1 | 7/2021 | Hong et al. | |

FOREIGN PATENT DOCUMENTS

| | | |
|---|---|---|
| KR | 10-1751885 B1 | 6/2017 |
| KR | 10-2021-0092408 A | 7/2021 |
| WO | WO 2020/127191 A1 | 6/2020 |

\* cited by examiner

DRUG DELIVERY DEVICE AND METHOD OF OPERATING THE DEVICE

CROSS-REFERENCE TO RELATED APPLICATIONS

This application claims the benefit under 35 USC § 119(a) of Korean Patent Application No. 10-2020-0100663, filed on Aug. 11, 2020, in the Korean Intellectual Property Office, the entire disclosure of which is incorporated herein by reference for all purposes.

BACKGROUND

Field

The following description relates to a drug delivery device and a method of operating the drug delivery device.

Description of Related Art

To avoid inconvenience and high medical costs when insulin or hormone formulations need to be repeatedly injected, there is a need to develop an implantable drug delivery system. Such an implantable drug release system may be broadly divided into a controlled drug release system and an activation modulated drug delivery system. The controlled drug release system slowly releases drug into a body mainly depending on an intrinsic rate of decomposition of a material in a body, and the activation modulated drug delivery system releases drug in response to a change in characteristics of a drug carrier due to stimulation from the inside and outside of a body.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In one general aspect, there is provided a drug delivery device including a light emitter disposed in a body to emit light based on a control signal, a drug reservoir configured to react to the light emitted from the light emitter and to release a drug, a photosensor configured to sense light passing through the drug reservoir, and a controller configured to monitor a degree to which the drug reservoir reacts to the light, based on an amount of light sensed by the photosensor.

The controller may be configured to determine an absorbance of the drug reservoir based on an amount of light emitted from the light emitter and the amount of light sensed by the photosensor, and to determine the degree to which the drug reservoir reacts to the light based on the absorbance.

The controller may be configured to determine an amount of drug released from the drug reservoir based on the degree to which the drug reservoir reacts to the light.

The controller may be configured to determine a change in a state of the drug reservoir based on a change in the absorbance of the drug reservoir over time.

The controller may be configured to control an amount of drug released from the drug reservoir by adjusting one or more of an exposure time and the amount of light emitted from the light emitter based on the degree to which the drug reservoir reacts to the light.

The controller may be configured to determine whether to replace the drug reservoir based on the degree to which the drug reservoir reacts to the light.

The controller may be configured to control any one or any combination of a wavelength, an exposure time, and an amount of light emitted from the light emitter, based on the control signal.

The drug reservoir may be configured to release the drug in response to light with an active wavelength corresponding to the drug reservoir being received from the light emitter.

The drug reservoir may be configured to release a drug corresponding to a wavelength of light received from the light emitter from among a plurality of drugs corresponding to different active wavelengths being included in the drug reservoir.

The light emitter may include at least one light source arranged to transmit light uniformly.

The drug reservoir may include one of a material conjugated to the drug via a photosensitive linker, an optogenetically engineered cell that secretes the drug in response to a change in an intracellular physiology by light, a photo-thermo-mechanical material that releases the drug using a material that generates heat or expands by light, and a photovoltaic material that secretes the drug in response to a change in magnetic properties by light.

The drug reservoir may be accommodated in a selective membrane configured to block an immunoreactive material to be generated in response to the drug delivery device being inserted into the body, to selectively pass the drug, and to selectively pass a material for maintaining the drug reservoir.

The controller may be configured to transmit, to an electronic device outside the drug delivery device, information about any one or any combination of the degree to which the drug reservoir reacts to the light, an amount of the drug released, and whether the drug reservoir needs to be replaced.

The drug delivery device may include an electrochemical sensor configured to sense a target molecule, wherein the controller is configured to control an amount of the drug released, by adjusting any one or any combination of an exposure time and an amount of light emitted from the light emitter based on a result obtained by sensing the target molecule in the electrochemical sensor.

The controller may be configured to determine a metabolic state in a body based on a concentration of the sensed target molecule and to determine whether to apply photostimulation to the drug reservoir based on the determined metabolic state.

The electrochemical sensor may be configured to sense a blood glucose level in the body, and the controller may be configured to control the light emitter to apply photostimulation that promotes a secretion of insulin from the drug reservoir, in response to the sensed blood glucose level exceeding a threshold level.

The controller may be configured to control the light emitted from the light emitter based on a signal received from any one or any combination of an electronic device outside the drug delivery device and prestored information.

The drug reservoir may include a replacement portal through which an additional drug is injectable from the outside of the drug delivery device.

The drug delivery device may include a heat sink pathway configured to discharge heat generated by the light emitter to the outside of the drug delivery device, the heat sink pathway being in contact with the light emitter.

In another general aspect, there is provided a method of operating a drug delivery device, the method including controlling a light emitter to emit light to a drug reservoir, the drug reservoir being configured to react to the light and release a drug, and monitoring a degree to which the drug reservoir reacts to the light, based on an amount of light passing through the drug reservoir and sensed by a photosensor, wherein the light emitter is disposed in a body.

In another general aspect, there is provided a drug delivery device including a light emitter to emit light based on a control signal; a drug reservoir disposed in a body, the drug reservoir being configured to release a drug based on the emitted light, a photosensor configured to sense light passing through the drug reservoir, and a controller configured to monitor the drug reservoir based on an amount of light sensed by the photosensor.

The controller may be configured to control any one or any combination of an exposure time, a wavelength and an amount of light emitted from the light emitter to adjust an amount of drug released from the drug reservoir.

A protective biocompatible layer may be disposed between the light emitter and the drug reservoir.

A change of reactivity of the drug reservoir may be calibrated after the drug reservoir is disposed into the body.

The two or more drugs may be placed in the drug reservoir, and the drug reservoir may be configured to selectively release one of the two or more drugs in response to a wavelength of the emitted light.

Other features and aspects will be apparent from the following detailed description, the drawings, and the claims.

Throughout the drawings and the detailed description, unless otherwise described or provided, the same drawing reference numerals will be understood to refer to the same elements, features, and structures. The drawings may not be to scale, and the relative size, proportions, and depiction of elements in the drawings may be exaggerated for clarity, illustration, and convenience.

DETAILED DESCRIPTION

The following detailed description is provided to assist the reader in gaining a comprehensive understanding of the methods, apparatuses, and/or systems described herein. However, various changes, modifications, and equivalents of the methods, apparatuses, and/or systems described herein will be apparent after an understanding of the disclosure of this application. For example, the sequences of operations described herein are merely examples, and are not limited to those set forth herein, but may be changed as will be apparent after an understanding of the disclosure of this application, with the exception of operations necessarily occurring in a certain order. Also, descriptions of features that are known in the art may be omitted for increased clarity and conciseness.

The features described herein may be embodied in different forms, and are not to be construed as being limited to the examples described herein. Rather, the examples described herein have been provided merely to illustrate some of the many possible ways of implementing the methods, apparatuses, and/or systems described herein that will be apparent after an understanding of the disclosure of this application.

The following structural or functional descriptions of examples disclosed in the present disclosure are merely intended for the purpose of describing the examples and the examples may be implemented in various forms. The examples are not meant to be limited, but it is intended that various modifications, equivalents, and alternatives are also covered within the scope of the claims.

Although terms of "first" or "second" are used to explain various components, the components are not limited to the terms. These terms should be used only to distinguish one component from another component. For example, a "first" component may be referred to as a "second" component, or similarly, and the "second" component may be referred to as the "first" component within the scope of the right according to the concept of the present disclosure.

It will be understood that when a component is referred to as being "connected to" another component, the component can be directly connected or coupled to the other component or intervening components may be present.

As used herein, the singular forms are intended to include the plural forms as well, unless the context clearly indicates otherwise. It should be further understood that the terms "comprises" and/or "comprising," when used in this specification, specify the presence of stated features, integers, steps, operations, elements, components or a combination thereof, but do not preclude the presence or addition of one or more other features, integers, steps, operations, elements, components, and/or groups thereof.

Hereinafter, examples will be described in detail with reference to the accompanying drawings, and like reference numerals in the drawings refer to like elements throughout.

Figure 1:
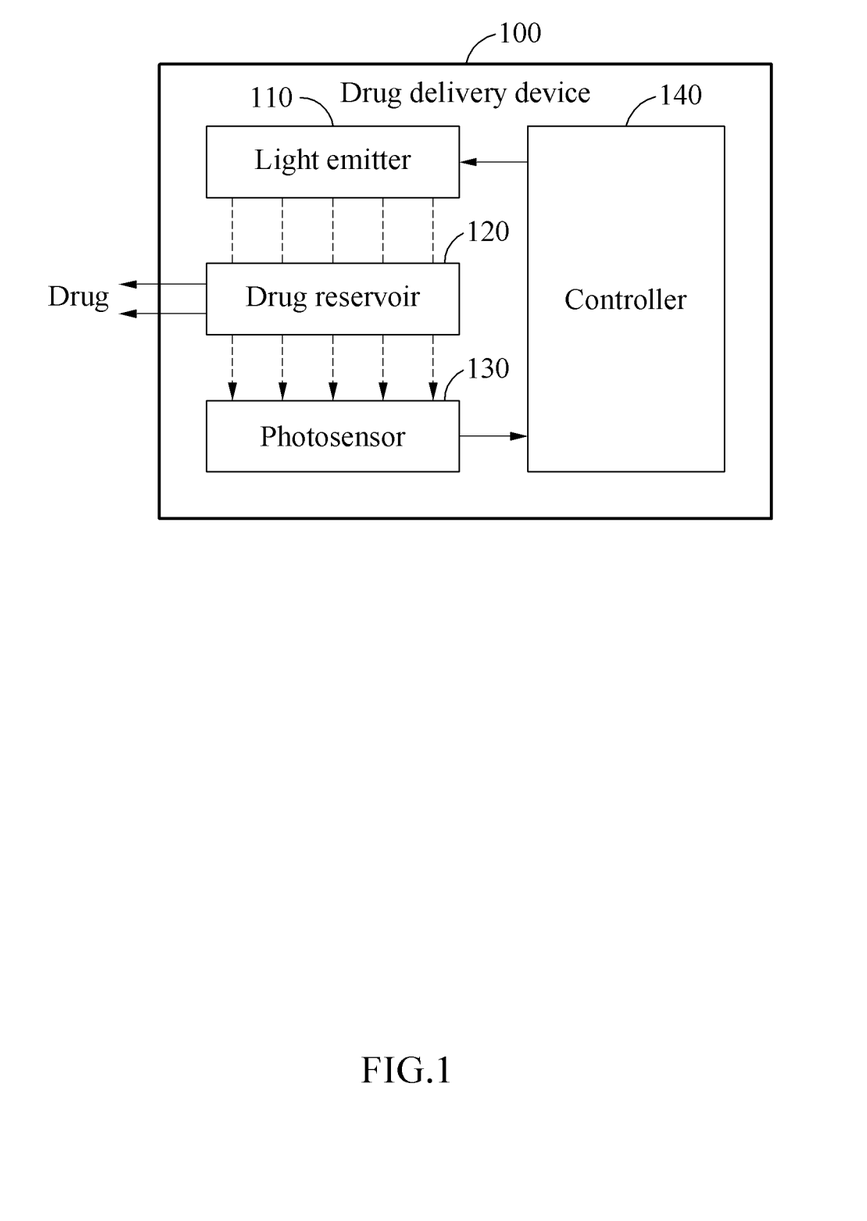
FIG. 1 illustrates an example of a drug delivery device.

FIG. 1 illustrates an example of a drug delivery device 100.

Referring to FIG. 1, the drug delivery device 100 includes a light emitter 110, a drug reservoir 120, a photosensor 130 and a controller 140. The drug delivery device 100 may be an implantable device configured to control drug release based on photostimulation, and may be implanted into a body to continuously or repeatedly release a drug.

The light emitter 110 may emit light based on a control signal from the controller 140. The light emitted from the light emitter 110 may act as photostimulation to the drug reservoir 120. Since the photostimulation is not stimulation to other cells in the body unlike other stimulation based on physics, chemistry and electricity, an unintended reaction in the body may be minimized by the photostimulation. Also, since a wavelength, an intensity and a range of light are freely controlled, the photostimulation may be applicable to various fields based on a type of photoprotein expressing cells. The light emitter 110 may be implanted into the body, so that various wavelengths may be utilized without a limitation. For example, the light emitter 110 may utilize various wavelengths, such as, for example, wavelengths ranging from ultraviolet (UV) and infrared (IR), however, examples are not limited thereto. All wavelengths capable of applying photostimulation to the drug reservoir 120 may be utilized without a limitation.

The light emitter 110 may emit light with at least one wavelength that induces a reaction of the drug reservoir 120. For example, the light emitter 110 may emit light of a predetermined active wavelength with an activity to the drug reservoir 120. The light emitter 110 may emit light based on an amount of light and/or an exposure time based on the control signal of the controller 140.

The drug reservoir 120 may react to the light emitted from the light emitter 110 and may release a drug. The drug reservoir 120 may be, for example, a material that absorbs light energy transmitted from the light emitter 110 and releases a drug into a body, and may react to a stimulation of light with a predetermined active wavelength. The drug reservoir 120 may include, for example, a material (for example, a photoresponsive polymer) conjugated to drug via a photosensitive linker, an optogenetically engineered cell that secretes a drug in response to a change in an intracellular physiology by light, a photo-thermo-mechanical material that releases a drug using a material that generates heat or expands by light, and a photovoltaic material that secretes a drug in response to a change in magnetic properties by light. The drug reservoir 120 may have a structure of a large surface area to facilitate a material exchange with the outside. Drug may be released into a body through a selective membrane, which will be described below. In the present specification, the drug reservoir 120 may also be referred to as a "therapeutic matrix", a "therapeutic material", or a "therapeutic agent".

A drug may refer to a material having a pharmacological activity which has an influence on diagnosis, treatment, alleviation, cure and prevention of diseases, or a physiological function of a body, such as a human body or an animal body. In the present description below reference may primarily be made to the human body, however, it is understood that the human body generally refers to any living body. The term "drug" used herein refers to a material having a pharmacological activity that has an influence on a physiological function of a human body, such as, for example, insulin. Insulin may be a material that needs to be continuously or repeatedly administered to treat, alleviate, cure, or prevent diabetes. However, the drug is not limited to insulin, and description of the present specification may also be applicable to other drugs.

The photosensor 130 may sense light passing through the drug reservoir 120. Light other than a portion of light used to release the drug by the drug reservoir 120 among the light emitted from the light emitter 110 may be sensed by the photosensor 130. The photosensor 130 may sense an amount of light passing through the drug reservoir 120 and may transfer the sensed amount of light to the controller 140.

The controller 140 may monitor a degree to which the drug reservoir 120 reacts to light based on the amount of light sensed by the photosensor 130. For example, the controller 140 may determine an absorbance of the drug reservoir 120 based on an amount of light emitted from the light emitter 110 and the amount of light sensed by the photosensor 130, and may determine the degree to which the drug reservoir 120 reacts to light, based on the determined absorbance. The drug may be released by a reaction of the drug reservoir 120 to photostimulation, and accordingly the controller 140 may determine an amount of drug to be released from the drug reservoir 120, based on reaction information of the drug reservoir 120.

The controller 140 may control any one or any combination of an exposure time, a wavelength and the amount of light emitted from the light emitter 110, based on the control signal, to adjust the amount of drug released from the drug reservoir 120. For example, when the amount of drug released from the drug reservoir 120 is less than a reference value, the controller 140 may increase the exposure time and the amount of light emitted from the light emitter 110. When the amount of drug released is greater than the reference value, the controller 140 may reduce the exposure time and the amount of light emitted from the light emitter 110.

Figure 2:
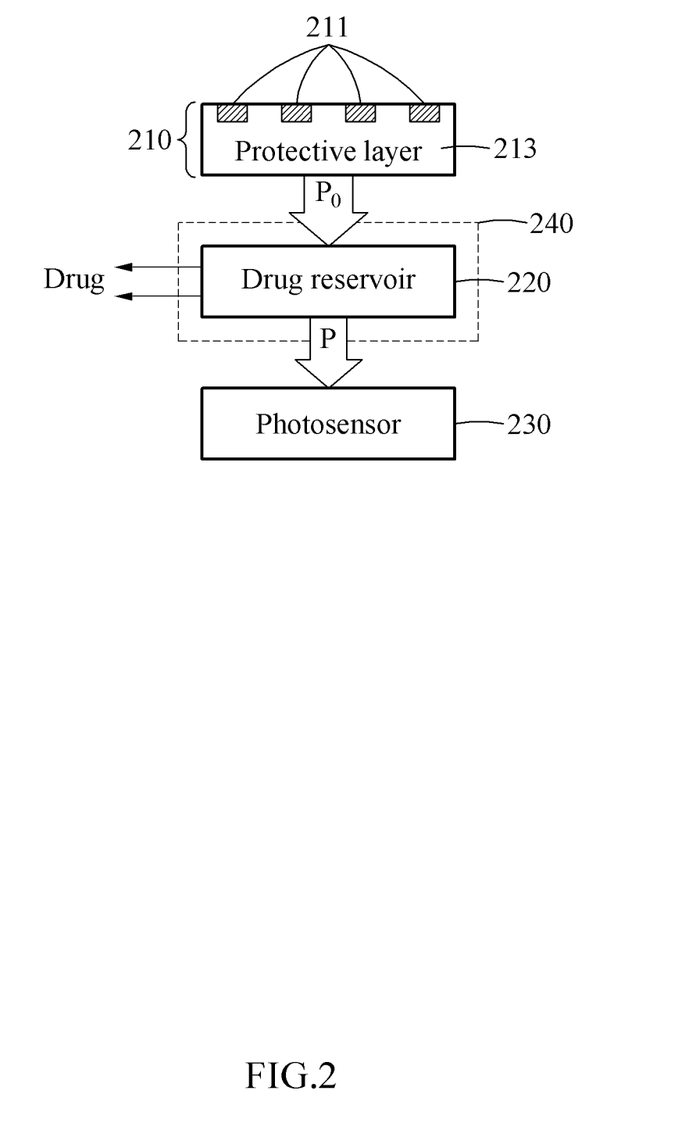
FIG. 2 illustrates an example of a drug reservoir.

FIG. 2 illustrates an example of a drug reservoir 220.

FIG. 2 illustrates an example of a process in which a photoreaction occurs in the drug reservoir 220.

A light emitter 210 may include light sources 211 arranged to allow light to be uniformly transferred to the drug reservoir 220. For example, the light emitter 210 may include light sources 211 (for example, light-emitting diodes (LEDs)) that are one-dimensionally or two-dimensionally arranged. One-dimensionally arranged light sources may be in a form of a line at equal intervals, and two-dimensionally arranged light sources may be in a form of a grid (for example, a triangular grid, or a square grid) at equal intervals.

A protective layer 213 included in the light emitter 210 may be a transparent material to protect the light sources 211. The protective layer 213 does not need to directly contact the drug reservoir 220, and accordingly the protective layer 213 may be biocompatible to a body.

The light emitter 210 may convert electric energy to light energy and may provide the light energy to the drug reservoir 220. The drug reservoir 220 may absorb a portion of the light energy received from the light emitter 210 and may release a drug. The remaining light energy passing through the drug reservoir 220 may be transferred to the photosensor 230 and is sensed by the photosensor 230.

The drug reservoir 220 that releases the drug in response to the photoreaction may be encapsulated by a selective membrane 240. The selective membrane 240 may block various immunoreactive materials that may be generated when the drug reservoir 220 is implanted into the body, to prevent the drug reservoir 220 from being damaged and destroyed due to immunoreactive materials. Also, the selective membrane 240 may pass a material (for example, nutrients, $O_2$, or body fluid) that is needed for a survival and maintenance of the drug reservoir 220 so that the material may be supplied to the drug reservoir 220. Also, the selective membrane 240 may pass a drug released due to the photoreaction of the drug reservoir 220 so that the drug may be delivered into the body. For example, when the drug is repeatedly released for a relatively long period of time, the drug reservoir 220 may be eroded or swelled, and an optogenetically engineered cell may move and deviate from a designated location. In this example, by preventing the above phenomenon, the selective membrane 240 may perform an important function to maintain a constant amount of drug to be released. Also, the selective membrane 240 may suppress deformation of a structure of the drug reservoir 220 to enable monitoring of a change in an absorbance for a relatively long period of time. In addition, the selective membrane 240 may suppress translocation of a toxic material or malignant cells. The selective membrane 240 may be a nano-porous membrane that selectively passes a material with a relatively small molecular weight.

The photosensor 230 may sense an amount of light passing through the drug reservoir 220. When the drug reservoir 220 absorbs and reacts to light energy, the amount of light sensed by the photosensor 230 may become less than the amount of light emitted from the light emitter 210, which may allow a degree of a reaction of the drug reservoir 220 to be monitored. The photoreaction in the drug reservoir 220 may be expressed by Equation 1 shown below.

$$A = \log \frac{P_0}{P} = \varepsilon c l \quad \text{[Equation 1]}$$

In Equation 1, A denotes an absorbance, $P_0$ denotes an amount of light emitted from the light emitter 210 and transferred to the drug reservoir 220, and P denotes an amount of light that passes the drug reservoir 220 and that is sensed by the photosensor 230. Also, $\varepsilon$ denotes a molar absorptivity that is a material-specific value indicating an amount of light to be absorbed per 1 mol of the drug reservoir 220, c denotes a concentration of the drug reservoir 220, and l denotes a length of an optical path through which the drug reservoir 220 passes.

Since light is emitted from the light emitter 210 based on a control signal, $P_0$ may be known, and P may be sensed by the photosensor 230. Also, $\varepsilon$ and l may correspond to predetermined values based on the drug reservoir 220. Thus, the concentration of the drug reservoir 220 may be obtained using Equation 1. Based on a characteristic that the concentration of the drug reservoir 220 decreases when an amount of drug released from the drug reservoir 220 increases, a change in a state of the drug reservoir 220 may be determined based on a change in the concentration due to a change in the absorbance. Also, a difference between the amounts $P_0$ and P may be used for a drug release by the photoreaction of the drug reservoir 220, and accordingly the degree of the reaction of the drug reservoir 220 may be determined based on the difference between the amounts $P_0$ and P. Furthermore, the amount of drug released from the drug reservoir 220 may be determined based on the degree of the reaction of the drug reservoir 220.

When the exposure time and/or the amount of light emitted from the light emitter 210 are adjusted based on the degree of the reaction of the drug reservoir 220, a constant amount of drug to be released from the drug reservoir 220 may be maintained. Thus, a closed-loop type drug delivery device capable of maintaining a constant amount of drug to be released for a relatively long period of time may be provided.

For example, when all drugs included in the drug reservoir 220 are released and no further photoreaction occurs, a relatively large amount of light may be received to the photosensor 230, and a controller may determine that the drug reservoir 220 needs to be replaced.

To more accurately monitor a reaction of the drug reservoir 220 to light, a calibration may be performed to analyze a change of reactivity of the drug reservoir 220 based on Equation 1 immediately after the drug reservoir 220 is initially inserted into a body.

Structurally, in an example, the light emitter 210, the drug reservoir 220 and the photosensor 230 may be arranged in a straight line in consideration of straightness of light, so that light emitted from the light emitter 210 may pass through the drug reservoir 220 to reach the photosensor 230.

Figure 3:
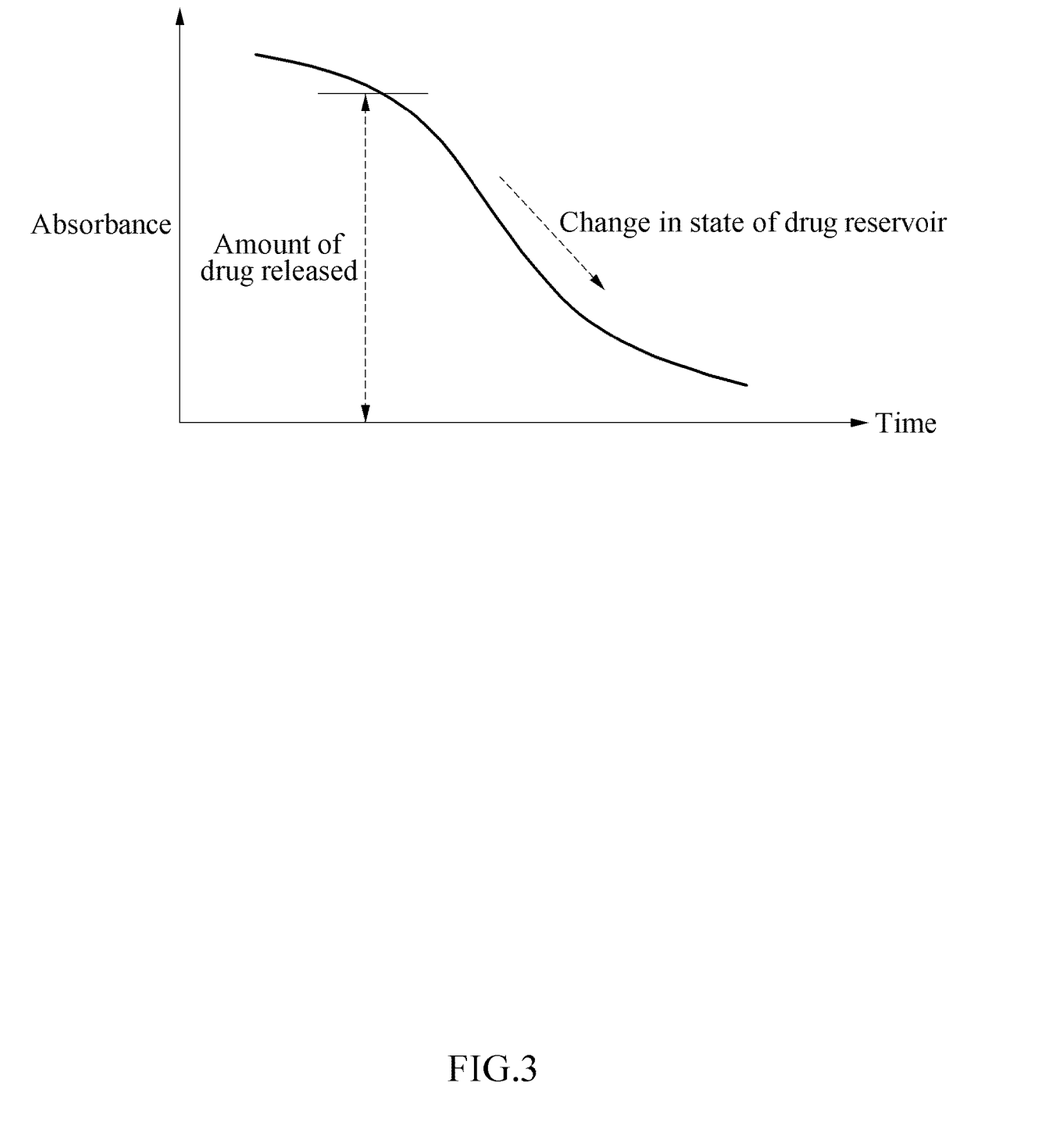
FIG. 3 illustrates an example of a process of monitoring a drug reservoir based on an absorbance.

FIG. 3 illustrates an example of a process of monitoring a drug reservoir based on an absorbance.

FIG. 3 illustrates a change in the absorbance. As described above, the absorbance may be determined based on an amount $P_0$ of light emitted from a light emitter and transmitted to the drug reservoir and an amount P of light passing through the drug reservoir and sensed by a photosensor. A portion of light provided to the drug reservoir may be used for a photoreaction and the remaining light may be sensed by the photosensor, and thus an amount of drug released from the drug reservoir may be determined based on a value of the absorbance. Also, the amount of drug released from the drug reservoir may correspond to a degree to which the drug reservoir reacts to photostimulation.

When a small amount of drug remains in the drug reservoir due to a release of the drug for a relatively long period of time, a photoreaction of the drug reservoir may be weakened. When the photoreaction becomes weakened, the amount P may become close to the amount $P_0$. In other words, the absorbance may gradually decrease, and a change in a state of the drug reservoir (for example, a reduction in a concentration of the drug reservoir) may be determined based on a change in the absorbance.

Figure 4:
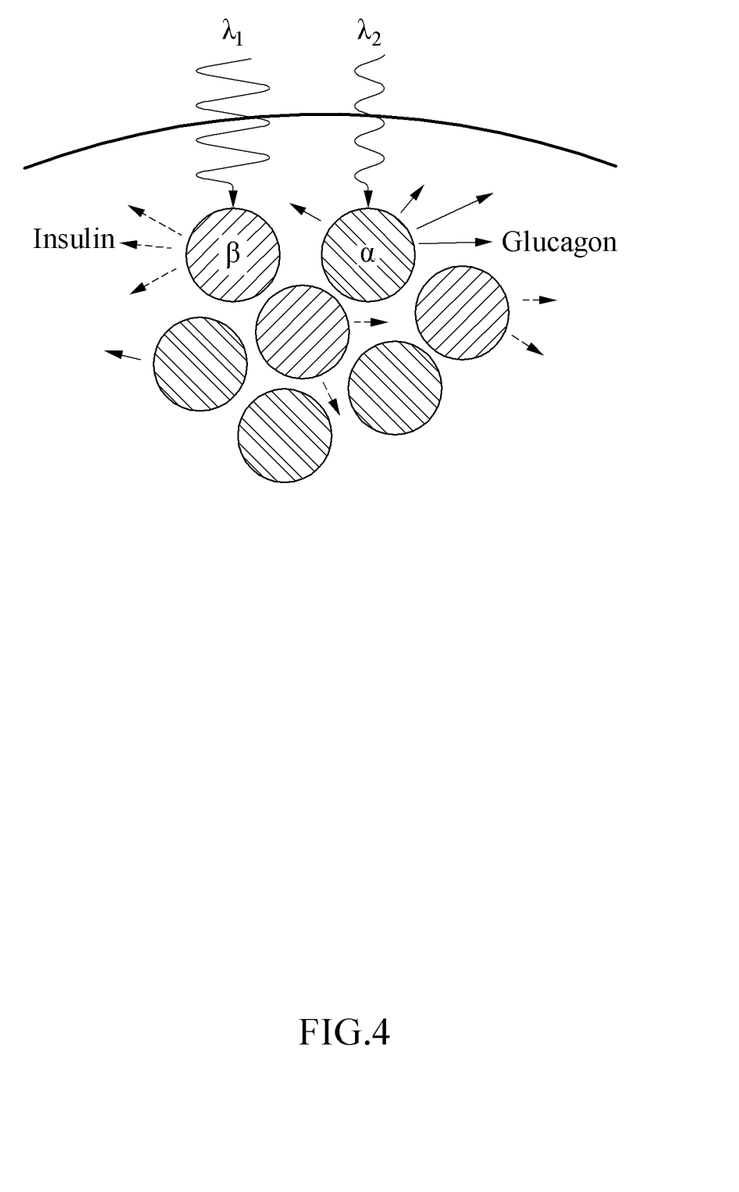
FIG. 4 illustrates an example of a drug release using a plurality of wavelengths.

FIG. 4 illustrates an example of a drug release using a plurality of wavelengths.

In FIG. 4, a plurality of drugs may be selectively released based on a first wavelength $\lambda_1$ and a second wavelength $\lambda_2$. Depending on examples, a drug reservoir may include the plurality of drugs, for example, insulin and glucagon. The glucagon may be a material that acts opposite to insulin. When light with the first wavelength $\lambda_1$ is incident on the drug reservoir, the drug reservoir may react to the light with the first wavelength $\lambda_1$ and may release insulin to a body. When light with the second wavelength $\lambda_2$ is incident on the drug reservoir, the drug reservoir may react to the light with the second wavelength $\lambda_2$ and may release glucagon to the body. Thus, by controlling a wavelength of light emitted from a light emitter, a required drug among the plurality of drugs may be selectively provided. Although two wavelengths are illustrated in FIG. 4 for convenience of description, various numbers of wavelengths may be used without a limitation.

Figure 5:
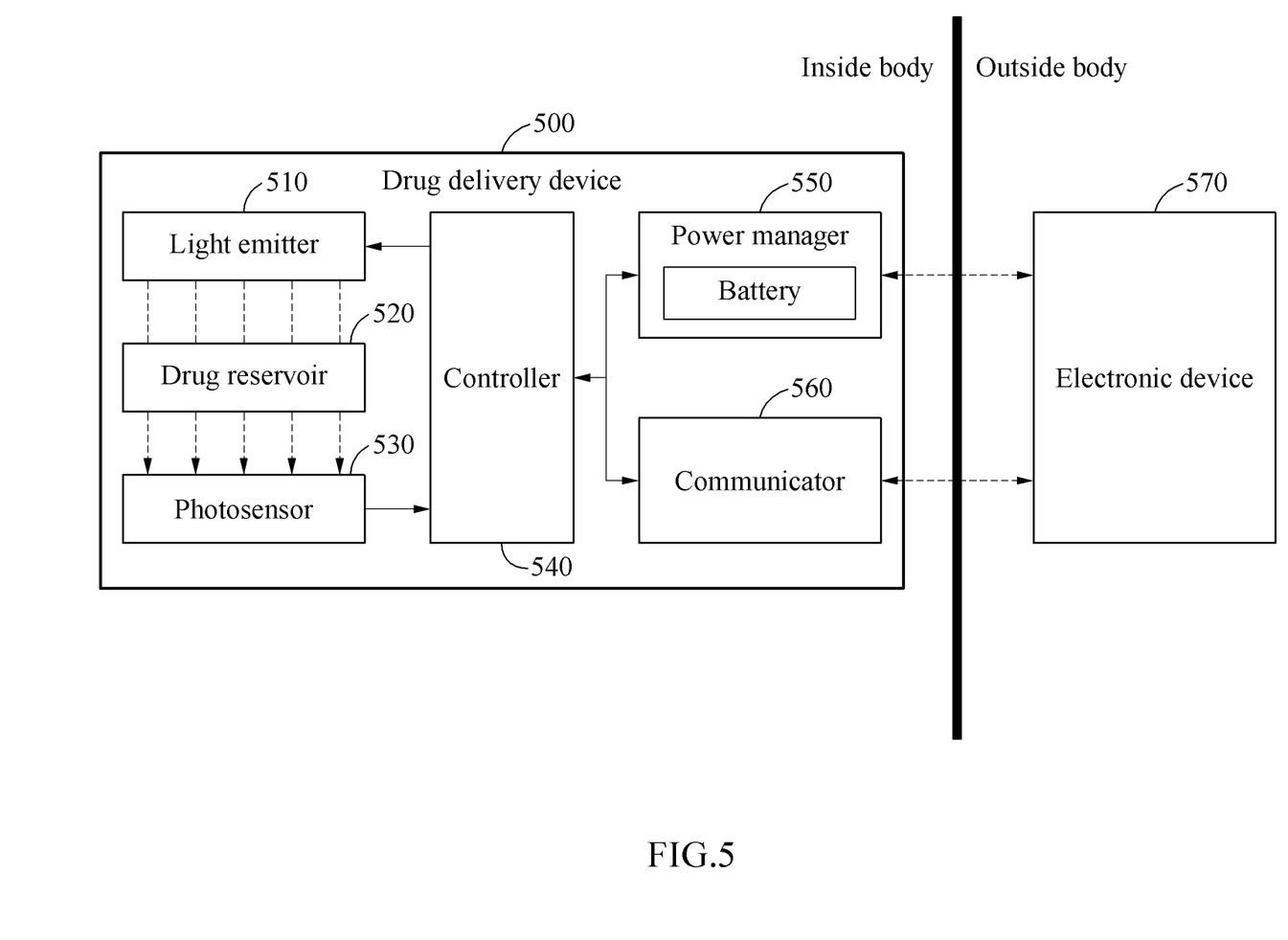
FIGS. 5 and 6 illustrate examples of operations of a drug delivery device and an electronic device.
Figure 6:
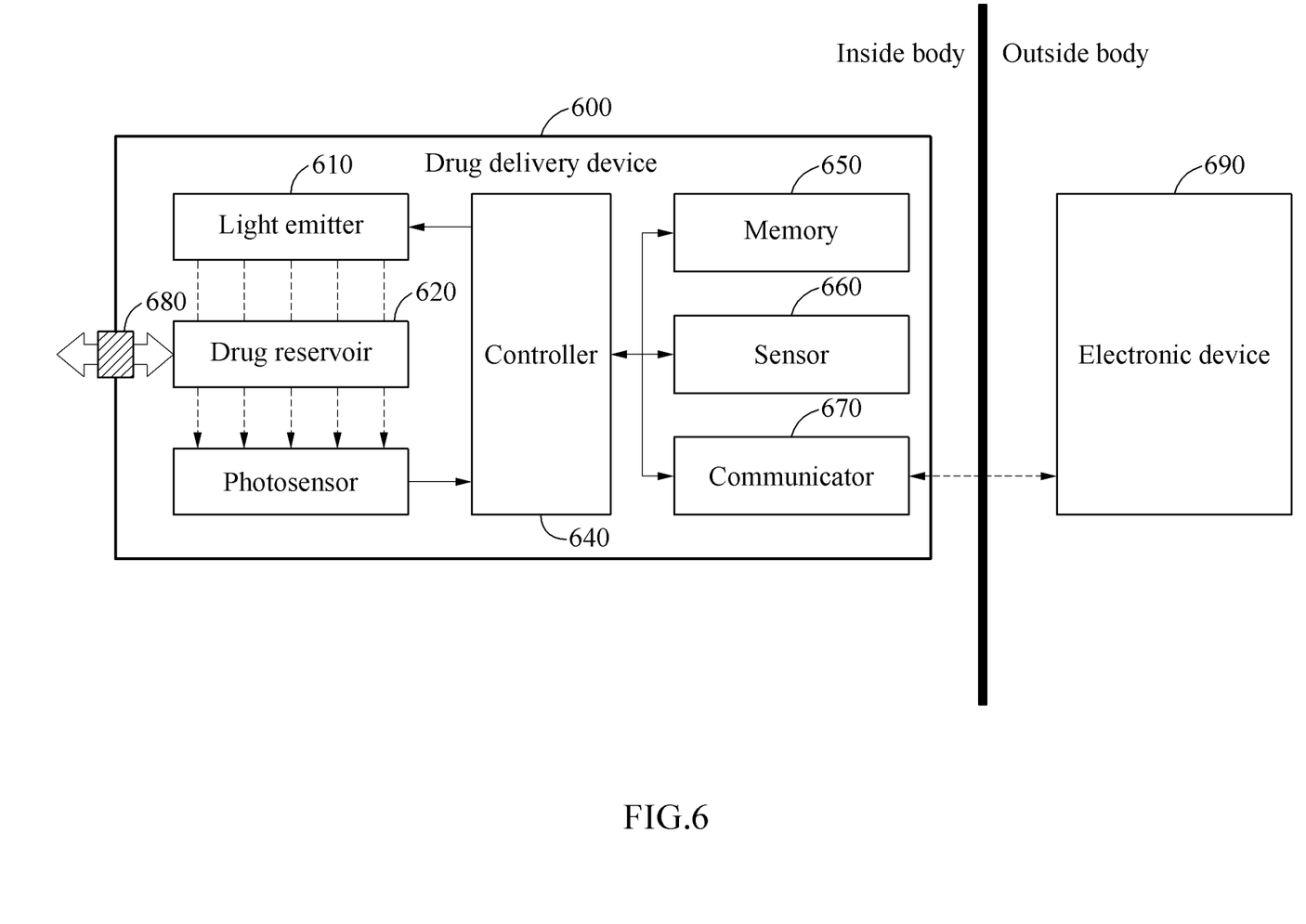

FIGS. 5 and 6 illustrate examples of operations of a drug delivery device and an electronic device.

Referring to FIG. 5, a drug delivery device 500 may include a light emitter 510, a drug reservoir 520, a photosensor 530, a controller 540, a power manager 550, and a communicator 560. The above description is also applicable to the light emitter 510, the drug reservoir 520, the photosensor 530 and the controller 540, and accordingly further description is not repeated herein.

The power manager 550 may provide power to the drug delivery device 500, and may include a battery. Also, the power manager 550 may receive power wirelessly from an electronic device 570, to provide the power to the drug delivery device 500 or charge the battery. The electronic device 570 may be located outside a body.

The communicator 560 may wirelessly communicate with the electronic device 570. For example, the communicator 560 may transmit, to the electronic device 570, information about any one or any combination of a degree of a reaction of the drug reservoir 520, an amount of drug released from the drug reservoir 520, whether the drug reservoir 520 needs to be replaced, an amount of power remaining in the battery, and a scheduled photostimulation schedule. The communicator 560 may communicate with the electronic device 570, based on various wireless communication schemes, such as, for example, Bluetooth low energy (BLE), medical implant communication service (MICS), or a near field communication (NFC).

The electronic device 570 may be a device controlled by a user into which the drug delivery device 500 is implanted and/or medical personnel who diagnose and treat a disease of the user. The electronic device 570 may include, for example, various computing devices such as a smartphone, a tablet, a laptop or a personal computer (PC), various wearable devices such as a smartwatch or smart glasses, various home appliances such as a smart speaker, a smart television (TV) or a smart refrigerator, a smart vehicle, a smart kiosk, or an Internet of things (IoT) device.

The drug delivery device 500 may be a photostimulation-based artificial pancreas device implanted in a patient with diabetes. The drug reservoir 520 may include optogenetically engineered pancreatic beta-cells, and may secrete insulin based on light with an active wavelength provided from the light emitter 510. The drug delivery device 500 may have a simpler device structure than an electrical stimulation system, may provide quantitative stimulation for exactly a desired time, and may monitor reactivity of beta-cells in real time.

FIG. 6 illustrates examples of controlling photostimulation.

In an example, a drug delivery device 600 may further include a memory 650. Photostimulation output from a light emitter 610 may be controlled based on setting information stored in the memory 650. For example, the memory 650 may store information about a cycle to output photostimulation, an amount of light and an exposure time, and the light emitter 610 may output photostimulation based on settings stored in the memory 650.

Also, the drug delivery device 600 may further include a sensor 660. The sensor 660 may be an electrochemical sensor configured to sense a target molecule. For example, the electrochemical sensor may be a type of a transducer, and may include a material (for example, an enzyme) that generates electricity by chemically reacting to a target molecule (for example, blood glucose), and an electrode to which the material is applied or that is in contact with or connected to the material. However, examples are not limited to the electrochemical sensor.

A controller 640 may electrochemically monitor a concentration of a target molecule in a body using the electrochemical sensor. The controller 640 may adjust an exposure time and/or an amount of light emitted from the light emitter 610, based on a result obtained by sensing the target molecule in the sensor 660. The controller 640 may determine a metabolic state in the body based on a concentration of the sensed target molecule, and may determine whether to apply photostimulation to the drug reservoir 620 based on the determined metabolic state. The metabolic state may be classified into a hyperglycemia state, a normal state and a hypoglycemia state. For example, the sensor 660 may sense a blood glucose level in the body, and the controller 640 may control the light emitter 610 to apply photostimulation that promotes a secretion of insulin of the drug reservoir 620 to the drug reservoir 620 in response to the sensed blood glucose level exceeding a threshold level.

The drug delivery device 600 may apply, to the drug reservoir 620, photostimulation corresponding to a signal received via a communicator 670 from an electronic device 690 that is located outside the body. An input of a user and/or medical personnel may be received via the communicator 670 from the electronic device 690, and photostimulation corresponding to the input may be applied to the drug reservoir 620.

Also, the drug delivery device 600 may include a replacement portal 680 to periodically replace or refill a drug. When a photoreaction in the drug reservoir 620 is weakened or no further photoreaction occurs due to a release of drug for a relatively long period of time, a new drug may be injected into the drug reservoir 620 through the replacement portal 680 without a need for a surgery to replace the drug delivery device 600. Thus, it is possible to minimize a surgery by extending a period of use of the drug delivery device 600 implanted into the body.

Figure 7:
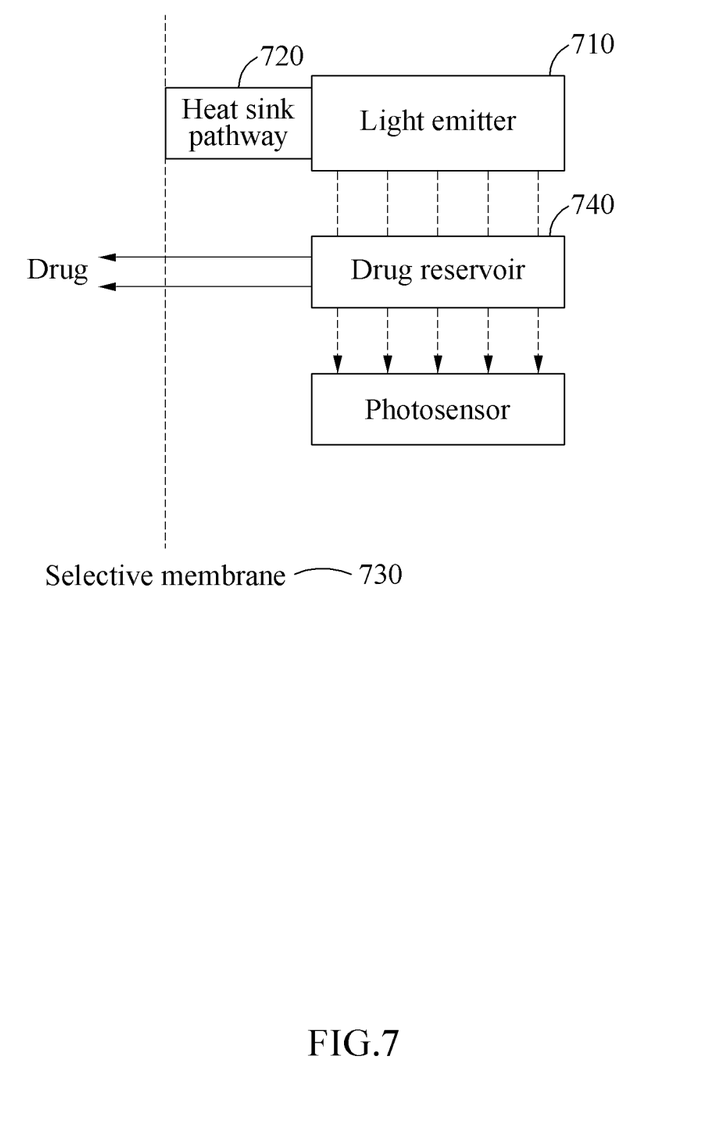
FIG. 7 illustrates an example of a heat sink pathway.

FIG. 7 illustrates an example of a heat sink pathway 720.

Referring to FIG. 7, a light emitter 710 may be in contact with the heat sink pathway 720 and may transfer heat generated in response to the light being emitted from the light emitter 710 to a site near a selective membrane 730, so that the heat may be discharged from a drug delivery device. Thus, it is possible to prevent a performance from being reduced or prevent a drug reservoir 740 from malfunctioning due to the heat generated in the light emitter 710. For example, the heat sink pathway 720 may include a metal with a high thermal conductivity and may be configured with a structure in which heat is efficiently transmitted.

Figure 8:
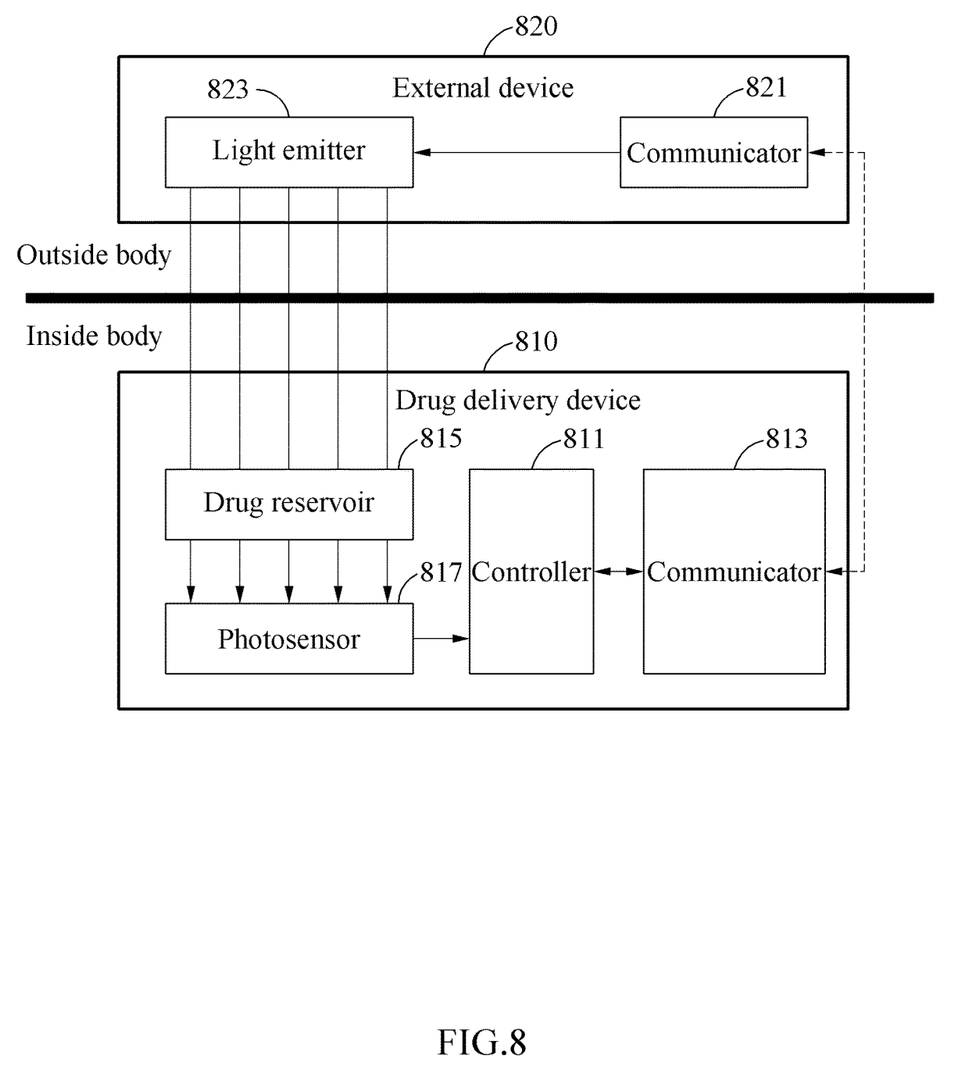
FIG. 8 illustrates another example of a drug delivery device.

FIG. 8 illustrates an example of a drug delivery device 810.

Referring to FIG. 8, a light emitter 823 may be included in an external device 820. A power manager, a sensor and a memory have been described above, and accordingly description thereof is not repeated herein for convenience of description.

The external device 820 may be located adjacent to the drug delivery device 810 by pairing with the drug delivery device 810. A communicator 813 of the drug delivery device 810 and a communicator 821 of the external device 820 may exchange information via a wireless communication. When a photostimulation is requested in a controller 811, a control signal for the photostimulation may be transmitted to the light emitter 823 via the wireless communication. Light emitted from the light emitter 823 based on the control signal may be transmitted to a drug reservoir 815 through human tissues. The above description may be applicable to operations, for example, a light reaction in the drug reservoir 815 and sensing of light that penetrates a photosensor 817, and accordingly further description of the operations is not repeated herein.

Figure 9:
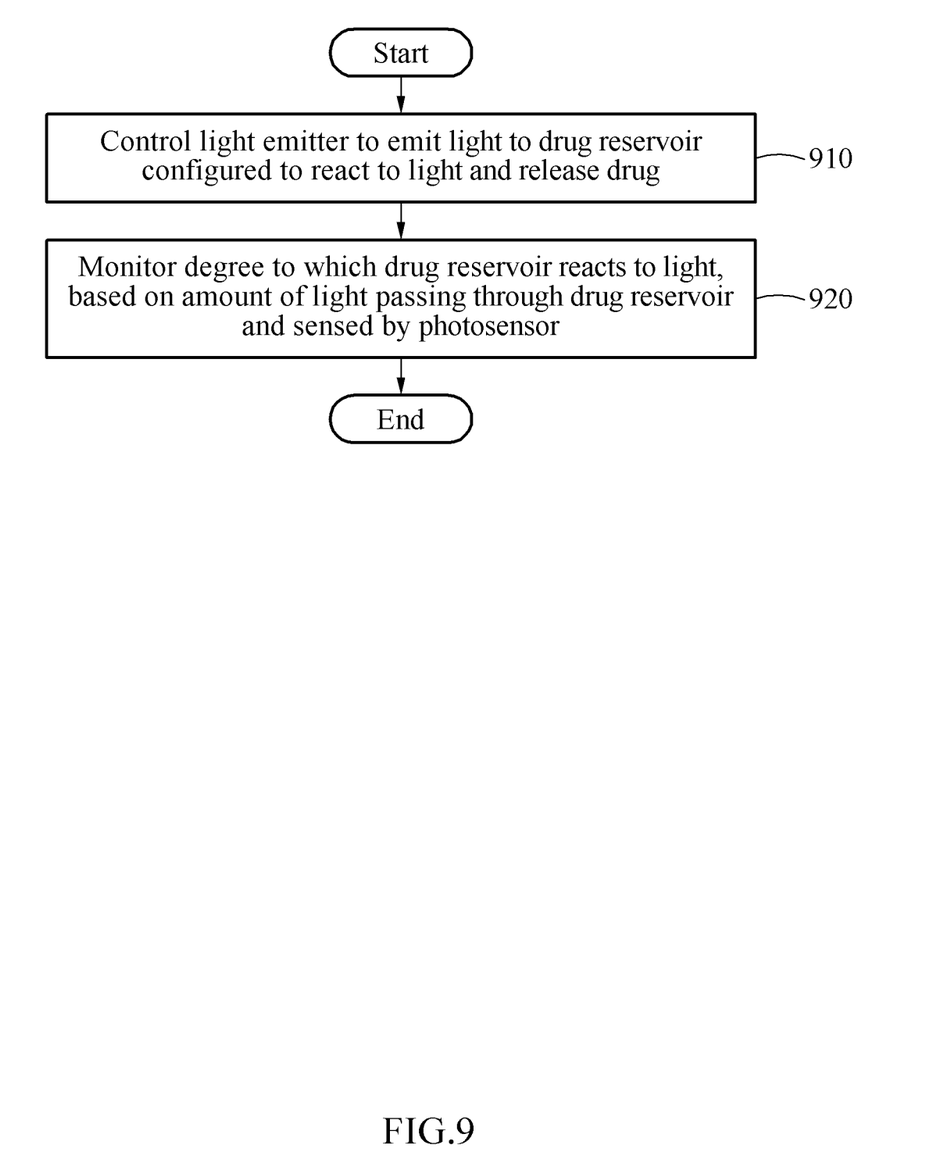
FIG. 9 illustrates an example of a method of operating a drug delivery device.

FIG. 9 illustrates an example of a method of operating a drug delivery device. The operations in FIG. 9 may be performed in the sequence and manner as shown, although the order of some operations may be changed or some of the operations omitted without departing from the spirit and scope of the illustrative examples described. Many of the operations shown in FIG. 9 may be performed in parallel or concurrently. One or more blocks of FIG. 9, and combinations of the blocks, can be implemented by special purpose hardware-based computer, such as a processor, that perform the specified functions, or combinations of special purpose hardware and computer instructions. In an example, the operating method of FIG. 9 may be performed by a processor included in the drug delivery device. In addition to the description of FIG. 9 below, the descriptions of FIGS. 1-8 are also applicable to FIG. 9, and are incorporated herein by reference. Thus, the above description may not be repeated here.

In operation 910, the drug delivery device controls a light emitter to emit light to a drug reservoir that is configured to react to the light and release a drug. In operation 920, the drug delivery device monitors a degree to which the drug reservoir reacts to the light, based on an amount of light that passes through the drug reservoir and that is sensed by a photosensor. The light emitter may be inserted into a body.

According to examples, a drug delivery device may be an implantable closed-loop type photostimulation drug release system capable of performing light-based stimulation and monitoring at the same time. The drug delivery device may have fewer side effects than implantable drug release systems based on other stimulation, and may monitor an amount of drug to be released with a high accuracy in real time, and thus the drug delivery device may be applicable to various devices for treatment. Also, the drug delivery device may be used for treatment of disease conditions requiring repeated administration as needed, and may be applicable to, for example, an implantable medical device for treating diabetes, a hormone treatment device, or an obesity treatment device.

The controller 140, controller 540, power manager 550, communicator 560, controller 640, communicator 670, controller 811, communicator 813, communicator 821, and other apparatuses, units, modules, devices, and other components described herein are implemented by hardware components. Examples of hardware components that may be used to perform the operations described in this application where appropriate include controllers, sensors, generators, drivers, memories, comparators, arithmetic logic units, adders, subtractors, multipliers, dividers, integrators, and any other electronic components configured to perform the operations described in this application. In other examples, one or more of the hardware components that perform the operations described in this application are implemented by computing hardware, for example, by one or more processors or computers. A processor or computer may be implemented by one or more processing elements, such as an array of logic gates, a controller and an arithmetic logic unit, a digital signal processor, a microcomputer, a programmable logic controller, a field-programmable gate array, a programmable logic array, a microprocessor, or any other device or combination of devices that is configured to respond to and execute instructions in a defined manner to achieve a desired result. In one example, a processor or computer includes, or is connected to, one or more memories storing instructions or software that are executed by the processor or computer. Hardware components implemented by a processor or computer may execute instructions or software, such as an operating system (OS) and one or more software applications that run on the OS, to perform the operations described in this application. The hardware components may also access, manipulate, process, create, and store data in response to execution of the instructions or software. For simplicity, the singular term "processor" or "computer" may be used in the description of the examples described in this application, but in other examples multiple processors or computers may be used, or a processor or computer may include multiple processing elements, or multiple types of processing elements, or both. For example, a single hardware component or two or more hardware components may be implemented by a single processor, or two or more processors, or a processor and a controller. One or more hardware components may be implemented by one or more processors, or a processor and a controller, and one or more other hardware components may be implemented by one or more other processors, or another processor and another controller. One or more processors, or a processor and a controller, may implement a single hardware component, or two or more hardware components. A hardware component may have any one or more of different processing configurations, examples of which include a single processor, independent processors, parallel processors, single-instruction single-data (SISD) multiprocessing, single-instruction multiple-data (SIMD) multiprocessing, multiple-instruction single-data (MISD) multiprocessing, multiple-instruction multiple-data (MIMD) multiprocessing, a controller and an arithmetic logic unit (ALU), a DSP, a microcomputer, an FPGA, a programmable logic unit (PLU), a central processing unit (CPU), a graphics processing unit (GPU), a neural processing unit (NPU), or any other device capable of responding to and executing instructions in a defined manner.

The methods that perform the operations described in this application are performed by computing hardware, for example, by one or more processors or computers, implemented as described above executing instructions or software to perform the operations described in this application that are performed by the methods. For example, a single operation or two or more operations may be performed by a single processor, or two or more processors, or a processor and a controller. One or more operations may be performed by one or more processors, or a processor and a controller, and one or more other operations may be performed by one or more other processors, or another processor and another controller. One or more processors, or a processor and a controller, may perform a single operation, or two or more operations.

Instructions or software to control a processor or computer to implement the hardware components and perform the methods as described above are written as computer programs, code segments, instructions or any combination thereof, for individually or collectively instructing or configuring the processor or computer to operate as a machine or special-purpose computer to perform the operations performed by the hardware components and the methods as described above. In one example, the instructions or software include machine code that is directly executed by the processor or computer, such as machine code produced by a compiler. In an example, the instructions or software includes at least one of an applet, a dynamic link library (DLL), middleware, firmware, a device driver, an application program storing the method of operating a drug delivery device. In another example, the instructions or software include higher-level code that is executed by the processor or computer using an interpreter. Programmers of ordinary skill in the art can readily write the instructions or software based on the block diagrams and the flow charts illustrated in the drawings and the corresponding descriptions in the specification, which disclose algorithms for performing the operations performed by the hardware components and the methods as described above.

The instructions or software to control a processor or computer to implement the hardware components and perform the methods as described above, and any associated data, data files, and data structures, are recorded, stored, or fixed in or on one or more non-transitory computer-readable storage media. Examples of a non-transitory computer-readable storage medium include read-only memory (ROM), random-access programmable read only memory (PROM), electrically erasable programmable read-only memory (EEPROM), random-access memory (RAM), dynamic random access memory (DRAM), static random access memory (SRAM), flash memory, non-volatile memory, CD-ROMs, CD-Rs, CD+Rs, CD-RWs, CD+RWs, DVD-ROMs, DVD-Rs, DVD+Rs, DVD-RWs, DVD+RWs, DVD-RAMs, BD-ROMs, BD-Rs, BD-R LTHs, BD-REs, blue-ray or optical disk storage, hard disk drive (HDD), solid state drive (SSD), flash memory, a card type memory such as multimedia card micro or a card (for example, secure digital (SD) or extreme digital (XD)), magnetic tapes, floppy disks, magneto-optical data storage devices, optical data storage devices, hard disks, solid-state disks, and any other device that is configured to store the instructions or software and any associated data, data files, and data structures in a non-transitory manner and providing the instructions or software and any associated data, data files, and data structures to a processor or computer so that the processor or computer can execute the instructions.

While this disclosure includes specific examples, it will be apparent after an understanding of the disclosure of this application that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner, and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. A drug delivery device comprising:
   a light emitter configured to be disposed in a body to emit light to a drug reservoir based on a control signal, such that a portion of the emitted light passes through the drug reservoir, wherein the light emitter is disposed above the drug reservoir;
   the drug reservoir configured to be disposed in the body to react to the light emitted from the light emitter and to release a drug into the body;
   a photosensor configured to sense the portion of the emitted light passing through the drug reservoir,
   wherein the photosensor is disposed below the drug reservoir such that the drug reservoir is located between the light emitter and the photosensor, and the light emitter and the photosensor are arranged in a straight line, and
   wherein a first layer includes the light emitter having plural light sources disposed in a form of a grid, and a second layer, below the first layer, includes the photosensor; and
   a controller configured to:
   determine an absorbance of the drug reservoir based on an amount of light emitted from the light emitter and an amount of light sensed by the photosensor;
   determine a degree to which the drug reservoir reacts to the light based on the absorbance; and
   determine an amount of the drug to be released into the body from the drug reservoir, based on the degree of reaction information of the drug reservoir.

2. The drug delivery device of claim 1, wherein the controller is further configured to determine a change in a state of the drug reservoir based on a change in the absorbance of the drug reservoir over time.

3. The drug delivery device of claim 1, wherein the controller is further configured to control the amount of the drug released from the drug reservoir by adjusting one or more of an exposure time and the amount of light emitted from the light emitter based on the degree to which the drug reservoir reacts to the light.

4. The drug delivery device of claim 1, wherein the controller is further configured to determine whether to replace the drug reservoir based on the degree to which the drug reservoir reacts to the light.

5. The drug delivery device of claim 1, wherein the controller is further configured to control any one or any combination of a wavelength, an exposure time, and an amount of light emitted from the light emitter, based on the control signal.

6. The drug delivery device of claim 1, wherein the drug reservoir is further configured to release the drug in response to light with an active wavelength corresponding to the drug reservoir being received from the light emitter.

7. The drug delivery device of claim 1, wherein the drug reservoir is further configured to release a drug corresponding to a wavelength of light received from the light emitter from among a plurality of drugs corresponding to different active wavelengths being included in the drug reservoir.

8. The drug delivery device of claim 1, wherein the light emitter comprises at least one light source arranged to transmit light uniformly.

9. The drug delivery device of claim 1, wherein the drug reservoir comprises one of:
   a material conjugated to the drug via a photosensitive linker;
   an optogenetically engineered cell that secretes the drug in response to a change in an intracellular physiology by light;
   a photo-thermo-mechanical material that releases the drug using a material that generates heat or expands by light; and
   a photovoltaic material that secretes the drug in response to a change in magnetic properties by light.

10. The drug delivery device of claim 1, wherein the drug reservoir is accommodated in a selective membrane configured to block an immunoreactive material to be generated in response to the drug delivery device being inserted into the body, to selectively pass the drug, and to selectively pass a material for maintaining the drug reservoir.

11. The drug delivery device of claim 1, wherein the controller is further configured to transmit, to an electronic device outside the drug delivery device, information about any one or any combination of the degree to which the drug reservoir reacts to the light, the amount of the drug released, and whether the drug reservoir needs to be replaced.

12. The drug delivery device of claim 1, further comprising:
   an electrochemical sensor configured to sense a target molecule,
   wherein the controller is configured to control the amount of the drug released, by adjusting any one or any combination of an exposure time and an amount of light emitted from the light emitter based on a result obtained by sensing the target molecule in the electrochemical sensor.

13. The drug delivery device of claim 12, wherein the controller is further configured to determine a metabolic state in the body based on a concentration of the sensed target molecule and to determine whether to apply photostimulation to the drug reservoir based on the determined metabolic state.

14. The drug delivery device of claim 12, wherein
   the electrochemical sensor is configured to sense a blood glucose level in the body, and
   the controller is further configured to control the light emitter to apply photostimulation that promotes a secretion of insulin from the drug reservoir, in response to the sensed blood glucose level exceeding a threshold level.

15. The drug delivery device of claim 1, wherein the controller is further configured to control the light emitted from the light emitter based on a signal received from any one or any combination of an electronic device outside the drug delivery device and prestored information.

16. The drug delivery device of claim 1, wherein the drug reservoir comprises a replacement portal through which an additional drug is injectable from the outside of the drug delivery device.

17. The drug delivery device of claim 1, further comprising:
a heat sink pathway configured to discharge heat generated by the light emitter to the outside of the drug delivery device, the heat sink pathway being in contact with the light emitter.

18. A method of operating a drug delivery device, the method comprising:
controlling a light emitter to emit light to a drug reservoir such that a portion of the emitted light passes through the drug reservoir, wherein the light emitter is disposed above the drug reservoir, the drug reservoir being configured to react to the light and release a drug into a body;
determining a degree to which the drug reservoir reacts to the light based on an absorbance of the drug reservoir; and
determine an amount of the drug to be released into the body from the drug reservoir, based on the degree of reaction information of the drug reservoir,
wherein the absorbance is determined based on an amount of light emitted from the light emitter and an amount of light passing through the drug reservoir and sensed by a photosensor, and
wherein the drug delivery device, the light emitter and the drug reservoir are configured to be disposed in the body, and
wherein the photosensor is disposed below the drug reservoir such that the drug reservoir is located between the light emitter and the photosensor, and the light emitter and the photosensor are arranged in a straight line, and
wherein a first layer includes the light emitter having plural light sources disposed in a form of a grid, and a second layer, below the first layer, includes the photosensor.

19. A drug delivery device comprising:
a light emitter to emit light to a drug reservoir based on a control signal, such that a portion of the emitted light passes through the drug reservoir, wherein the light emitter is disposed above the drug reservoir;
a drug reservoir configured to be disposed in a body, the drug reservoir being configured to release a drug into the body based on the emitted light;
a photosensor configured to sense the portion of the emitted light passing through the drug reservoir,
wherein the photosensor is disposed below the drug reservoir such that the drug reservoir is located between the light emitter and the photosensor, and the light emitter and the photosensor are arranged in a straight line, and
wherein a first layer includes the light emitter having plural light sources disposed in a form of a grid, and a second layer, below the first layer, includes the photosensor; and
a controller configured to:
determine an absorbance of the drug reservoir based on an amount of light emitted from the light emitter and an amount of light sensed by the photosensor;
determine a degree to which the drug reservoir reacts to the light based on the absorbance; and
determine an amount of the drug to be released into the body from the drug reservoir, based on the degree of reaction information of the drug reservoir.

20. The drug delivery device of claim 19, wherein the controller is further configured to control any one or any combination of an exposure time, a wavelength and an amount of light emitted from the light emitter to adjust the amount of the drug released from the drug reservoir.

21. The drug delivery device of claim 19, wherein a protective biocompatiable layer is disposed between the light emitter and the drug reservoir.

22. The drug delivery device of claim 19, wherein a change of reactivity of the drug reservoir is calibrated after the drug reservoir is disposed into the body.

23. The drug delivery device of claim 19, where two or more drugs are placed in the drug reservoir, and the drug reservoir is further configured to selectively release one of the two or more drugs in response to a wavelength of the emitted light.

* * * * *